United States Patent [19]

Hanai et al.

[11] Patent Number: 5,445,938
[45] Date of Patent: Aug. 29, 1995

[54] ANTI-DCC GENE PRODUCT SPECIFIC MONOCLONAL ANTIBODY

[75] Inventors: Nobuo Hanai, Kanagawa; Shozo Baba, Shizuoka; Tadachika Ozawa, Shizuoka, all of Japan

[73] Assignee: Kyowa Hakko Kogyo Co., Ltd., Tokyo, Japan

[21] Appl. No.: 80,809

[22] Filed: Jun. 24, 1993

[30] Foreign Application Priority Data

Jun. 25, 1992 [JP] Japan .................. 4-167101

[51] Int. Cl.$^6$ .......................... G01N 33/574
[52] U.S. Cl. .................. 435/7.23; 436/64; 436/813; 530/388.8; 530/388.85
[58] Field of Search .......... 435/7.23, 240.27; 530/388.8, 388.85; 436/64, 813

[56] References Cited

FOREIGN PATENT DOCUMENTS

84/03564 9/1984 WIPO.
90/05180 5/1990 WIPO.
91/04490 4/1991 WIPO.
91/09964 7/1991 WIPO.

OTHER PUBLICATIONS

Boyd, J. et al., *Proc Annu Meet Am Assoc Cancer Res*, vol. 32, A 1838 1991.

*Monoclonal Antibody Technology*, Ailsa Campbell, Edited by R. H. Burdon, Elsevier, 1987, pp. 29–30.
The New England Journal of Medicine, vol. 319, No. 9, pp. 525–532.
Eur. J. Biochem., vol. 159, pp. 529–534 (1986).
Proc. Natl. Acad. Sci., USA, vol. 87, pp. 7555–7559 (1990).
Journal of Cell Science, vol. 101, 183–189 (1992).
Science, vol. 247, pp. 49–56, (1990).
Science, vol. 251, pp. 1366–1370 (1991).
Science, vol. 244, pp. 217–221 (1989).
Science, vol. 253, pp. 665–669 (1991).

*Primary Examiner*—Toni R. Scheiner
*Attorney, Agent, or Firm*—Nixon & Vanderhye

[57] ABSTRACT

This invention relates to monoclonal antibodies capable of specifically reacting with a peptide encoded by tumor suppressor gene DCC gene and to hybridomas capable of producing such monoclonal antibodies. In particular, the invention relates to mouse monoclonal antibody KM890 belonging to the IgG3 subclass, which is specifically reactive with a DCC gene DCC-2, and to a hybridoma KM890 capable of producing the monoclonal antibody KM890.

The monoclonal antibodies of this invention which are specifically reactive with DCC gene products can be used in immunohistochemical staining, quantitative determination of DCC gene products and the like, as well as in cancer diagnosis.

1 Claim, 1 Drawing Sheet

ANTI-DCC GENE PRODUCT SPECIFIC MONOCLONAL ANTIBODY

FIELD OF THE INVENTION

This invention relates to monoclonal antibodies specifically reactive with a peptide encoded by a tumor suppressor gene, DCC. The monoclonal antibodies of this invention are useful in cancer diagnosis and the like.

BACKGROUND OF THE INVENTION

Vogelstein et al. have examined chromosomes in familial polyposis patients from the benign adenoma stage to the cancer stage and have detected the disappearance in heterozygosity (deletion of allele) in chromosomes 5, 17, 18 and 22 (New Engl. J. Med., 319, 525–532, 1988), thus indicating the possible existence of a familial polyposis-related tumor suppressor gene in these deleted chromosomes. Thereafter, it was confirmed that the tumor suppressor gene located on chromosome 17P was identical with the P53 gene, a known oncogene (Science, 244, 217–221, 1989). Subsequently, a DCC (deleted in colorectal carcinoma) gene was identified as a tumor suppressor gene located on chromosome 18q (Science, 247, 49–56, 1990), and the isolation of a MCC (mutated in colorectal cancer) gene and an APC (adenomatous polyposis) gene located on chromosome 5q was reported (Science, 251, 1366–1370, 1991; and Science, 253, 665–669, 1991).

The DCC gene has a considerably large size (2 to 3 mega bases), and a cloned 370 kb fragment thereof is considered to have at least 8 exons. The corresponding mRNA is from 1 to 12 kb, and its expression has been found in the large intestine, the brain and the like. In large bowel cancer cells, it has been confirmed that certain mutations such as deletions, point mutations, insertions and the like occur in the DCC gene. In the future, the function of the DCC gene as an antioncogene will be elucidated, for example, by introducing the DCC gene into DCC gene-deficient cancer cells.

It is presumed that the function of the peptide encoded by the DCC gene (referred to as "DCC gene product" hereinafter) involves intercellular communication, because its deduced amino acid sequence shares homology with a cell adhesion molecule, N-CAM (neural cell adhesion molecule). However, many aspects of the localization, function and the like of tile DCC gene product are still unclear because of the lack of availability of antibodies which react specifically with the DCC gene product.

Antibodies specific for the gene product of the tumor suppressor gene P53 located on chromosome 17P have been prepared (Eur. J. Biochem., 159,529–534, 1986), and it has been reported that cancer cells expressing large quantities of the P53 gene product stain positive using the abovedescribed antibodies in an immunohistochemical staining protocol (Proc. Natl. Acad. Sci. USA, 87, 7555–7559, 1990). In addition, it has been reported that a peptide encoded in the P53 gene (referred to as "P53 gene product" hereinafter) can be measured quantitatively by means of an enzyme immunoassay technique using antibodies to the P53 gene product (J. Cell Science, 101, 183–189, 1992).

Thus, the availability of antibodies specific for the DCC gene product would make possible not only immunohistochemical staining and quantitative determination of the DCC gene product but also cancer diagnosis and the like.

SUMMARY OF THE INVENTION

An object of the present invention is to provide monoclonal antibodies specific for the gene product of a tumor suppressor gene DCC and a method of diagnosing cancer using such an antibody.

The inventors of the present invention selected several partial amino acid sequences 10 to 30 amino acid residues in length from the amino acid sequence of a DCC gene product 750 amino acid residues in length which has been deduced from a known partial nucleotide sequence of the DCC gene (Science, 247, 49–56, 1990), and prepared synthetic peptides based on the thus selected partial amino acid sequences. An animal was immunized with a conjugate prepared from each of the thus prepared synthetic peptides and a carrier protein, and splenocytes from the immunized animal were fused with mouse myeloma cells to obtain hybridoma cell lines which were then screened in order to select for a hybridoma strain capable of producing a monoclonal antibody which reacts with the peptide used as an immunogen but not with peptides having different amino acid sequences. The thus selected hybridoma cell line was cultured in a medium or administered to an animal to cause an ascites tumor, and monoclonal antibodies isolated from the cultured broth or the tumor-caused ascitic fluid were subjected to screening to select for a monoclonal antibody which could be used as a first antibody in an immunohistochemical staining protocol in which cancer cells stained positively. It was found that the thus selected monoclonal antibody was specifically reactive with the DCC gene product and thus could be used to diagnose cancer using histological tissue examination and the like.

The present invention relates to a monoclonal antibody specifically reactive with a DCC gene product (referred to as "anti-DCC gene product monoclonal antibody" hereinafter), to a hybridoma capable of producing such an antibody, to a composition suitable for use in cancer diagnosis that contains the antibody as an active ingredient and to an antigen suitable for use in producing such antibodies.

Further objects and advantages of the present invention will become clear from the description that follows. All references cited herein are hereby incorporated by reference.

DETAILED DESCRIPTION OF THE INVENTION

Figure 1A:
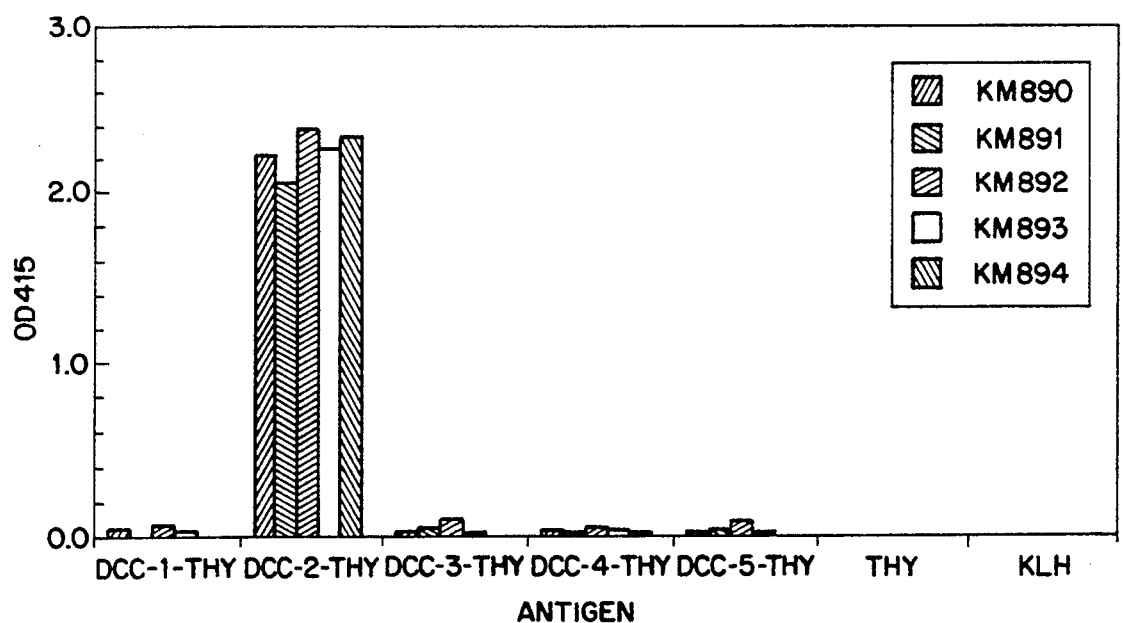
FIGS. 1a and 1b are groups showing reactivities of (a) monoclonal antibodies KM890 to KM894 and (b) monoclonal antibodies KM890 to KM894 and (b) monoclonal

The present invention relates, in general, to peptides of the DCC gene product, and to monoclonal antibodies specific therefor. In particular, the invention relates to partial peptides deduced from a known nucleotide sequence of the DCC gene and to monoclonal antibodies that react specifically therewith. Exemplary methods of making the peptides of the invention are described below, as are methods of preparing the monoclonal antibodies. Data relating to the peptide of SEQ ID NO:2 and to monoclonal antibodies specific therefor are set forth in the Examples that follow.

In addition to the peptides deduced from the known nucleotide sequence of the DCC gene, the invention also relates to peptides, and monoclonal antibodies specific therefor, encoded by DCC genes, the nucleotide sequence of which is mutated (e.g., by point mutation, insertion or deletion). For example, peptides bearing conservative substitutions (relative to the peptides deduced from the known nucloetide sequence of the DCC gene), and antibodies specific therefor, are within the scope of the invention.

It will be appreciated that while the invention relates to intact monoclonal antibodies specific for peptides of the DCC gene product, it also relates to antigen-binding fragments thereof. Such fragments can be prepared by enzyme digestion of the intact antibody using known methodologies (e.g., papain or pepsin digestion). Such fragments can be used in lieu of the intact antibodies in cancer diagnosis.

A method of producing the anti-DCC gene product monoclonal antibodies of this invention is described in further detail below.

(1) Synthesis of peptide antigen

The peptides having amino acid sequences represented by SEQ ID Nos:1 to 5 can be synthesized by a solid phase method using an automatic peptide synthesizer. A solid phase carrier to which the thus synthesized peptide has been linked is treated with hydrogen fluoride to liberate the peptide from the solid phase carrier and, at the same time, to remove protecting groups from the amino acid side chains. The thus obtained crude peptide is purified by high performance liquid chromatography (referred to as "HPLC" hereinafter) using a reverse phase column, and the purified product is used as a peptide antigen.

(2) Immunization of animals and preparation of antibody-producing cells

Mice, rats or hamsters of 3 to 20 weeks of age are immunized with a conjugate of the peptide antigen obtained in the above step (1) and a carrier protein such as Hemocyanine Keyhole Limpet (referred to as "KLH" hereinafter), bovine serum albumin, thyroglobulin, ovalbumin, human serum albumin or the like, and antibody-producing cells are collected from the spleen, lymph node or peripheral blood of the animals.

The immunization may be carried out by administering the antigen together with an appropriate adjuvant, such as complete Freund's adjuvant, or aluminum hydroxide gel plus pertussis vaccine, to the animals subcutaneously, intravenously or intraperitoneally.

Following the first antigen administration, the antigen is administered repeatedly 5 to 10 times at one- to two-week intervals. Three to seven days after each administration, a blood sample is taken from each animal from the venous plexus of the fundus of the eye, and the serum derived from the sample blood is tested, for example, by enzyme immunoassay (cf. *Antibodies—A Laboratory Manual,* Cold Spring Harbor Laboratory, 1988) to determine whether it is reactive with the antigen. A mouse, rat or hamster whose serum shows a sufficient antibody titer against the antigen used for immunization is used as a splenocyte source.

The spleen of the immunized mouse, rat or hamster is excised 3 to 7 days after the final administration of the antigen and splenocytes of the spleen are collected. That is, the spleen is cut to pieces in an MEM medium (Nissui Pharmaceutical Co., Ltd.), and cells are dissociated using forceps. After centrifugation (1,200 rpm, 5 minutes), the supernatant is discarded, and the sediment is treated with Tris-ammonium chloride buffer (pH 7.65) for 1 to 2 minutes to eliminate erythrocytes. The remaining cells are washed three times with MEM medium and the thus obtained splenocytes are used for cell fusion.

(3) Preparation of myeloma cells

Established mouse myeloma cell lines can be used for fusion with splenocytes. Thus, for instance, the 8-azaguanine-resistant mouse (BALB/c-derived) myeloma cell lines P3-X63Ag8-U1 (P3-U1) (*Current Topics in Microbiology and Immunology,* 18, 1–7, 1978), P3-NS1/1-Ag41 (NS-1) (*European J. Immunology,* 6, 511–519, 1976), SP2/O-Ag14 (SP-2) (*Nature,* 276, 269–270, 1978), P3-X63-Ag8653 (653) (*J. Immunology,* 123, 1548–1550, 1979)and P3-X63-Ag8 (X63) (*Nature,* 256, 495–497, 1975) may be used. These cell lines are subcultured in an 8-azaguanine medium [prepared by supplementing RPMI-1640 medium with glutamine (1.5 mM), 2-mercaptoethanol ($5\times10^{-5}$ M), gentamicin (10 $\mu$g/ml) and fetal calf serum (FCS) and further supplementing the resulting medium (referred to as "normal medium" hereinafter) with 8-azaguanine (15 $\mu$g/ml)]. Three to four days before cell fusion, subculture is performed in the normal medium to thereby ensure a cell number of not less than $2\times10^7$ cells on the day of cell fusion.

(4) Cell fusion

The antibody-producing cells obtained by immunization as described in the above step (2) and the myeloma cells obtained as described in the above step (3) are washed well with the MEM medium or PBS (1.83 g of disodium phosphate, 0.21 g of monopotassium phosphate and 7.65 g of sodium chloride per liter of distilled water, pH 7.2), and mixed in a proportion of 5 to 10 antibody-producing cells per myeloma cell, and the mixture is subjected to centrifugation (1,200 rpm, 5 minutes). The supernatant is discarded, the sediment (cells) is thoroughly resuspended, a mixture consisting of 2 g of polyethylene glycol-1,000 (PEG-1,000), 2 ml of MEM and 0.7 ml of dimethyl sulfoxide is added to the antibody-producing cells with stirring in an amount of 0.2 to 1 ml/$10^8$ cells at 37° C., then several 1 to 2 ml portions of MEM are added at 1- to 2-minute intervals, and the whole amount is made 50 ml by further addition of MEM. After centrifugation (900 rpm, 5 minutes), the supernatant is discarded, the cells are loosened gently and then suspended in 100 ml of an HAT medium [prepared by supplementing the normal medium with hypoxanthine ($10^{-4}$M), thymidine (1.5 $\times 10^{-5}$M) and aminopterine ($4\times10^{-7}$M)] by repeated drawing up into and discharging from a graduated pipette. This suspension is distributed in 100-$\mu$l portions into each well of 96-well incubation plates, and incubation is carried out in a 5% $CO_2$ incubator at 37° C. for 7 to 14 days.

After incubation, a portion of the culture supernatant is taken and subjected to enzyme immunoassay, for instance. Wells giving a supernatant capable of reacting with the peptide used as an immunogen but not with other peptides having different sequences are selected and subjected to cloning twice by the limiting dilution method [using an HT medium (HAT medium minus aminopterine) for the first cloning and the normal medium for the second]. Strains for which a high antibody titer is constantly observed are selected as anti-DCC gene product monoclonal antibody-producing hybridoma cell lines.

(5) Preparation of monoclonal antibodies

The anti-DCC gene product specific monoclonal antibody-producing hybridoma cells obtained in the above step (4) are intraperitoneally injected into 8- to 10-week-old mice or nude mice treated with pristane [by intraperitoneal administration of 0.5 ml of 2, 6, 10, 14-tetramethylpentadecane (pristane) followed by 2 weeks of feeding] at a dose of $2 \times 10^6$ to $5 \times 10^7$ cells per animal. The hybridoma causes an ascites tumor in 10 to 21 days. The ascitic fluid is collected from the mice, centrifuged (3,000 rpm, 5 minutes) to remove solid matter and, after salting out with 40–50% ammonium sulfate, passed through a DEAE-Sepharose column, a protein A column or a gel filtration column. Thereafter, IgG or IgM fractions are collected to give purified monoclonal antibodies.

The subclass of the antibody can be determined by enzyme immunoassay using a subclass typing kit. The amount of protein can be determined by the Lowry method, followed by calculation based on the optical density at 280 nm.

(6) Selection of anti-DCC gene product monoclonal antibodies

The monoclonal antibodies obtained in the above step (5) are used as first antibodies in the immunohistochemical staining method (*Antibodies—A Laboratory Manual*, Cold Spring Harbor Laboratory, 1988) to select monoclonal antibodies which provide positive staining of cancer cells in a tissue section. In this instance, it is desirable to select monoclonal antibodies which provide positive staining of not only a frozen tissue-derived tissue sections but also of tissue sections prepared from a formalin-fixed paraffin-embedded block.

An illustrative example of the anti-DCC gene product specific monoclonal antibody selected in the above manner is the anti-DCC gene product specific monoclonal antibody KM890 produced by the hybridoma cell line KM890. The hybridoma cell line KM890 has been deposited with the Fermentation Research Institute, Agency of Industrial Science and Technology, Japan, of 1–3, Higashi 1-chome, Tsukuba-shi, Ibaraki 305, Japan, since Jun. 16, 1992.under deposit number FERM BP-3889 and in accordance with the forms of the Budapest Treaty.

The monoclonal antibodies according to the present invention can be used as a composition suitable for cancer diagnosis. They may be formulated into an diagnostic composition together with at least one pharmaceutically acceptable carrier. For instance, the monoclonal antibodies are dissolved in physiological saline, an aqueous solution of glucose, lactose or mannitol and the like. The powder of the monoclonal antibodies for injection can be prepared by lyophilizing the monoclonal antibodies in accordance with the conventional method of mixing the lyophilized products with sodium chloride. The diagnostic composition may further contain additives conventionally used well known in the art of medical preparation, for example, pharmaceutically acceptable salts.

The anti-DCC gene product specific monoclonal antibody according to the present invention can be used for cancer diagnosis such as histological tissue examination and imaging. The histological tissue examination can be carried out using the monoclonal antibody of the present invention as described below.

Tissues obtained by operation and the like are embedded in paraffin to prepare specimens. A section of the paraffin-embedded specimen having a thickness of several micrometers is prepared using a microtome, put on a slide glass, treated with xylene to remove paraffin and then treated with ethanol to make the section hydrophilic. The resulting section is washed with PBS, subjected to blocking with methanol containing not more than 1% hydrogen peroxide and rabbit serum solution and the like. Then, the section is allowed to react with the purified monoclonal antibody (1–20 μg/ml) which serves as a first antibody at 4° C. for 10 hours or at room temperature for several hours. After washing with PBS, the resulting section is allowed to react with a second antibody labeled with biotin, peroxidase and the like at room temperature for 1 to 3 hours. When the second antibody is labeled with biotin, the section is allowed to react with peroxidase-labeled streptoavidin at room temperature for several hours and then, the section is subjected to color development using a diaminobenzene solution followed by chromosomal staining with Methyl Green, hematoxylin and the like. After dehydration and sealing, the section is observed with a microscope.

The cancer imaging using the monoclonal antibody of the present invention can be carried out as follows in accordance with the method described in "Diagnosis of Colorectal and Ovarian Carcinoma", edited by Robert T. Maguire arid Douglas Van Nostrand, Marcel Dekker, Inc.

The purified monoclonal antibody is digested with pepsin, papain and the like enzymes to gine F(ab')$_2$. The thus obtained F(ab')$_2$ is labeled with a radioactive material such as $^{121}$I, $^{111}$I or $^{99m}$Tc and intravenously administered to a cancer patient. Several hours to several days after the administration of the labeled F(ab')$_2$, the whole body of the patient is radiographed with a gamma camera. Since the F(ab')$_2$ labeled with the radioactive material accumaletes in cancer tissues, the cancer tissue portion is visualized in blacks in the radiograph. The cancer portion can be detected more clearly by pseudo color radiograph and the like.

The following examples are provided to further illustrate the present invention. It is to be understood, however, that the examples are for purposes of illustration only and are not intended as a definition of the limits of the present invention. In the following examples, peptide synthesis was carried out using a peptide synthesizer Model 430A (Applied Biosystems, Inc., Foster City, Calif., USA; referred to as "ABI" hereinafter) and reagents and solvents of ABI, based on the ABI's synthesis program. Condensation reaction of asparagine, glutamine and arginine was carried out by converting them into active esters using 1-hydroxybenzotriazole, and other amino acids under standard conditions as respective acid anhydrides. Physicochemical properties were measured using Hitachi M-80B for mass spectrometry and Waters pico tag for amino acid analysis.

EXAMPLE 1

(1) Synthesis of peptide antigen

Peptide antigens DCC-1, DCC-2, DCC-3, DCC-4 and DCC-5 having, respectively, the amino acid sequences shown in SEQ ID Nos. 1 to 5, were synthesized in the following manner.

(1-1) Synthesis of DCC-1

A 0.37 g portion of a carrier resin to which 0.25 mmol of t-Boc-Ile had been linked was put into a reaction vessel of an automatic synthesizer, and the following treatment and washing steps (i) to (v) were carried out in accordance with the ABI's synthesis program to obtain an isoleucine-linked carrier resin:

(i) treatment with a methylene chloride solution containing 33% trifluoroacetic acid for 80 seconds,
(ii) treatment with a methylene chloride solution containing 50% trifluoroacetic acid for 18.5 minutes,
(iii) three times of washing with methylene chloride,
(iv) two times of treatment with a methylene chloride solution containing 10% diisopropylethylamine, each for 1 minute, and
(v) five times of washing with dimethylformamide (DMF). The thus obtained isoleucine-linked carrier resin was further subjected to the following treatment and washing steps:
(vi) addition of 4 ml of a DMF solution containing 1.0 mmol of an acid anhydride corresponding to t-Boc-Thr(Bzl), and subsequent stirring in the reaction vessel for 18 minutes, and (vii) five times of washing with methylene chloride.

The thus obtained t-Boc-Thr(Bzl)-Ile-linked carrier resin was subjected to the above deprotection steps (i) to (v), to the condensation reaction step (vi) in which t-Boc-Pro-corresponding acid anhydride was used in place of t-Boc-Thr(Bzl), and then to the washing step (vii), thereby effecting synthesis of t-Boc-Pro-Thr(Bzl)-Ile on the carrier resin. The steps (i) to (vii) were repeated to obtain 1.09 g of the protected peptide-linked carrier resin. In this instance, t-Boc-Met, t-Boc-Pro, t-Boc-Glu(OBzl), t-Boc-Gly, t-Boc-Ile, t-Boc-Val, t-Boc-Glu(OBzl), t-Boc-Cys(4-CH3Bzl), t-Boc-Lys(Cl-Z), t-Boc-Leu(H2O), t-Boc-Leu(H2O), t-Boc-Val, t-Boc-Thr(Bzl), t-Boc-Asp(OBzl), t-Boc-Gly, t-Boc-Met, t-Boc-Phe and t-Boc-Ala were used in that order in the step (vi). After completion of the synthesis reaction, 1.09 g of the carrier resin thus obtained was mixed with 1.4 ml of anisole and the mixture was allowed to stand for 15 hours. Then, 15 ml of hydrogen fluoride was added to the mixture, followed by stirring for 1.2 hours in an ice bath. After removing hydrogen fluoride under a reduced pressure, the thus treated carrier resin was stirred in 100 ml of ethyl acetate for 0.5 hour and the carrier resin collected by filtration was stirred in 100 ml of 2M acetic acid for 1 hour. Thereafter, the carrier resin was removed by filtration, and the resulting filtrate was subjected to freeze drying to obtain 24 mg of a crude product. The thus obtained product was purified by HPLC using a reverse phase column (CAPCELL PAK C18 SG120, 30×250 mm). Elution was effected by a linear density gradient technique using 0.1% trifluoroacetic acid and acetonitrile, and fractions containing DCC-1 were detected at 220 nm and pooled. The pooled fraction was freeze-dried to obtain 26.0 mg of purified DCC-1.

Physiocochemical properties of DCC-1 are as follows.

Mass spectrometry (SIMS): 2263 (M+1) Amino acid analysis, found/(calculated): Asx, 1.0 (1); Glx, 2.2 (2); Thr, 2.0 (2); Ala, 1.0 (1); Pro, 2.2 (2); Val, 1.6 (2); Met, 2.0 (2); Ile, 1.7 (2); Leu, 2.1 (2); Phe, 1.1 (1); Lys, 1.0 (1); Cys, 0.8 (1)

(1-2) Synthesis of DCC-2

A protected peptide-linked carrier resin was obtained in a yield of 1.0 g by repeating the procedure of (1-1) except for using a t-Boc-Thr-linked carrier resin and t-Boc-amino acids as protected amino acids in the order of the amino acid sequence of DCC-2. The thus obtained carrier resin was treated in the same manner as described in (1-1), thereby yielding 443 mg of a crude product. Thereafter, entire portion of the product was purified using HPLC to yield 107 mg of DCC-2.

Physiocochemical properties of DCC-2 are as follows. Mass spectrometry: 2261 (M+1) Amino acid analysis, found/(calculated): Asn, 1.9 (2); Glx, 1.0 (1); Ser, 2.9 (3); Gly, 2.1 (2); Arg, 3.1 (3); Thr, 1.0 (1); Ala, 2.1 (2); Pro, 2.0 (2); Tyr, 0.9 (1); Ile, 1.9 (2); Leu, 1.0 (1); Cys, 1.0 (1)

(1-3) Synthesis of DCC-3

A protected peptide-linked carrier resin was obtained in a yield of 1.1 g by repeating the procedure of (1-1) except for using a t-Boc-Val-linked carrier resin and t-Boc-amino acids as protected amino acids in the order of the amino acid sequence of DCC-3. The thus obtained carrier resin was treated in the same manner as described in (1-1), thereby yielding 512 mg of a crude product. Thereafter, a 400 mg portion of the product was purified using HPLC to yield 144 mg of DCC-3.

Physiocochemical properties; of DCC-3 are as follows. Mass spectrometry: 2387 (M+1) Amino acid analysis, found/(calculated): Asx, 2.9 (3); Glx, 3.2 (3); Ser, 1.0 (1); Gly, 1.1 (1); Arg, 3.1 (3); Thr, 2.9 (3); Pro, 1.1 (1); Val, 0.9 (1); Leu, 1.0 (1); Phe, 2.9 (3) (1-4) Synthesis of DCC-4

A protected peptide-linked carrier resin was obtained in a yield of 0.9 g by repeating the procedure of (1-1) except for using a t-Boc-Val-linked carrier resin and t-Boc-amino acids as protected amino acids in the order of the amino acid sequence of DCC-4. The thus obtained carrier resin was mixed with 0.9 ml of 1,2-ethanedithiol, 0.9 ml of dimethyl sulfide and 0.23 ml of anisole and then treated in the same manner as described in (1-1), thereby yielding 399 mg of a crude product. Thereafter, the entire product was purified using HPLC to yield 50 mg of DCC-4.

Physiocochemical properties of DCC-4 are as follows.

Mass spectrometry: 2160 (M+1) Amino acid analysis, found/(calculated): Asx, 1.0 (1); Glx, 4.2 (4); Ser, 1.9 (2); Gly, 2.1 (2); Thr, 1.0 (1); Ala, 2.0 (2); Pro, 2.1 (2); Tyr, 0.9 (1); Val, 2.0 (2); Ile, 0.9 (1); Lys, 0.9 (1); Trp, 1.0 (1)

(1-5) Synthesis of DCC-5

A protected peptide-linked carrier resin was obtained in a yield of 1.2 g by repeating the procedure of (1-1) except for using a t-Boc-Ala-linked carrier resin and t-Boc-amino acids as protected amino acids in the order of the amino acid sequence of DCC-5. The entirety of the thus obtained carrier resin was mixed with 5.9 ml of DMF and 0.5 ml of thiophenol, and the resulting mixture was stirred for 1 hour at room temperature. The thus treated carrier resin was collected by filtration, washed with 20 ml of DMF, 20 ml of water, 20 ml of ethanol and 20 ml of methylene chloride in that order, put into a reaction vessel of an automatic synthesizer and then subjected to the aforementioned deprotection steps (i) to (v) of the procedure (1-1) in accordance with the de-Boc program, thereby yielding 0.92 g of carrier resin. The thus obtained carrier resin was treated in the same manner as described in (1-1) to yield 406 mg of a crude product. Thereafter, the entire product was purified using HPLC, thereby yielding 115.4 mg of DCC-5.

Physiocochemical properties of DCC-5 are as follows.

Mass spectrometry: 2461 (M+1) Amino acid analysis, found/(calculated): Glx, 3.2 (3); Gly, 2.1 (2); His, 1.0 (1); Arg, 4.0 (4); Thr, 4.0 (4); Tyr, 0.9 (1); Met, 0.9 (1); Ile, 0.9 (1); Leu, 1.1 (1); Lys, 1.9 (2)

(2) Immunization of animals and preparation of antibody-producing cells

After allowing N-(m-maleimidobenzoyloxy)succinimide (referred to as "MBS" hereinafter; Nakarai Tesque) to react with KLH or cycloglobulin, the reaction product was purified by a Sephadex G25 column. The thus purified product was mixed witch each of the peptides synthesized in (1) in a ratio of 5:1 and a peptide-KLH conjugate was formed using a known method (Cell, 28, 477–487, 1982). The conjugate was dialyzed against PBS and used as an antigen. BALB/c female mice (5 mice for each peptide) were given 100 µg of one of the peptide-KLH conjugates together with 2 mg of an aluminum gel and $1 \times 10^9$ cells of pertussis vaccine (Chiba Serum Institute). After 2 weeks, weekly administration of 100 µg of the peptide-KLH conjugates was started. After 5 administrations in all, blood was sampled from the venous plexus of the fundus of the eye and tested for serum antibody titer by an enzyme immunoassay described below. Three days after the final immunization, the spleen was excised from a mouse showing a sufficient antibody titer.

The spleen was cut to pieces in MEM medium (Nissui Pharmaceutical Co., Ltd.) and cells were dissociated using forceps. After centrifugation (1,200 rpm, 5 minutes), the supernatant was discarded, and the sediment was treated with Tris-ammonium chloride buffer (pH 7.65) for 1 to 2 minutes in order to eliminate erythrocytes. The cells were then washed three times with MEM and used for cell fusion.

Enzyme immunoassay

A 1 to 50 µg/ml solution of the peptide prepared as described in the above step (1) was distributed in 0 to 100 µl aliquots into wells of a 96-well plate for EIA (Greiner), and the plate was kept for 10 hours at 4° C. for coating of the antigen. Then, a PBS solution containing 1% BSA (BSA-PBS) was distributed in 100 to 200 µl aliquots into the wells. The plate was kept at room temperature for 1 to 2 hours or at 4° C. for 10 to 30 hours for blocking the protein-binding residues remaining on the plate. The BSA-PBS was then discarded, the plate was washed well with PBS, and samples (mouse sera, hybridoma culture supernatants, or purified monoclonal antibodies) diluted with BSA-PBS were distributed in 20 to 100 µl aliquots into the wells, each as a first antibody. The plate was kept at room temperature for 2 to 3 hours or at 4° C. for 10 hours and then washed well with PBS or a PBS solution containing 0.05% Tween-20. A peroxidase-labeled anti-mouse immunoglobulin antibody (DAKO) or peroxidase-labeled anti-rat immunoglobulin antibody (DAKO), as a second antibody, was distributed in 50 to 100 µl aliquots per well, and the plate was kept at room temperature for 2 hours. After thorough washing of the plate with PBS, color development was caused using an ABTS substrate solution [prepared by dissolving 550 mg of 2,2'-azinobis(3-ethylbenzothiazoline-6-sulfonic acid) diammonium salt in 1 liter of 0.1M citrate buffer (pH 4.2) and adding, just prior to use, hydrogen peroxide to the solution to a concentration of 1 µl/ml], and optical density ($OD_{415\ mm}$).

(3) Preparation of mouse myeloma cells

The 8-azaguanine-resistant mouse myeloma cell line P3-U1 was cultured in the normal medium and not less than $2 \times 10^7$ cells were present at the time of cell fusion and were subjected to cell fusion as a parent strain.

(4) Hybridoma formation

The mouse splenocytes obtained as described in the above step (2) and the myeloma cells obtained as described in the above step (3) were mixed in a ratio of 10:1, and the mixture was centrifuged (1,200 rpm, 5 minutes). The supernatant was discarded, and the precipitated cells were thoroughly resuspended. A mixed solution of 2 g of polyethylene glycol-1,000 (PEG-1,000), 2 ml of MEM and 0.7 ml of dimethyl sulfoxide was added to the cells with stirring at 37° C. in an amount of 0.2 to 1 ml per $10^8$ mouse splenocytes, followed by addition of several 1 to 2-ml aliquots of MEM at 1 to 2-minute intervals. Thereafter, the total volume was made 50 ml by addition of MEM. After centrifugation (900 rpm, 5 minutes), the supernatant was discarded, and the cells were gently loosened and then gently suspended in 100 ml of HAT medium by repeated drawing up into and discharging from a graduated pipette.

The suspension was distributed in 100-µl portions into each well of a 96-well incubation plate and incubation was performed in a 5% $CO_2$ incubator at 37° C. for 10 to 14 days. After culturing, each culture supernatant was examined by the enzyme immunoassay to select wells which reacted with a conjugate of cycloglobulin and the peptide used as the immunogen (referred to as "peptide-THY" hereinafter) but not with other peptide-THYs in which the peptide was not the one used as an immunogen and, for them, cloning was repeated twice using HT medium and the normal medium in place of HAT medium, respectively. In this way, hybridomas were selected that produced monoclonal antibodies reactive with the peptide-THY in which the peptide was used as an immunogen but not with the peptide-THY in which the peptide was not the immunogen.

Figure 1B:
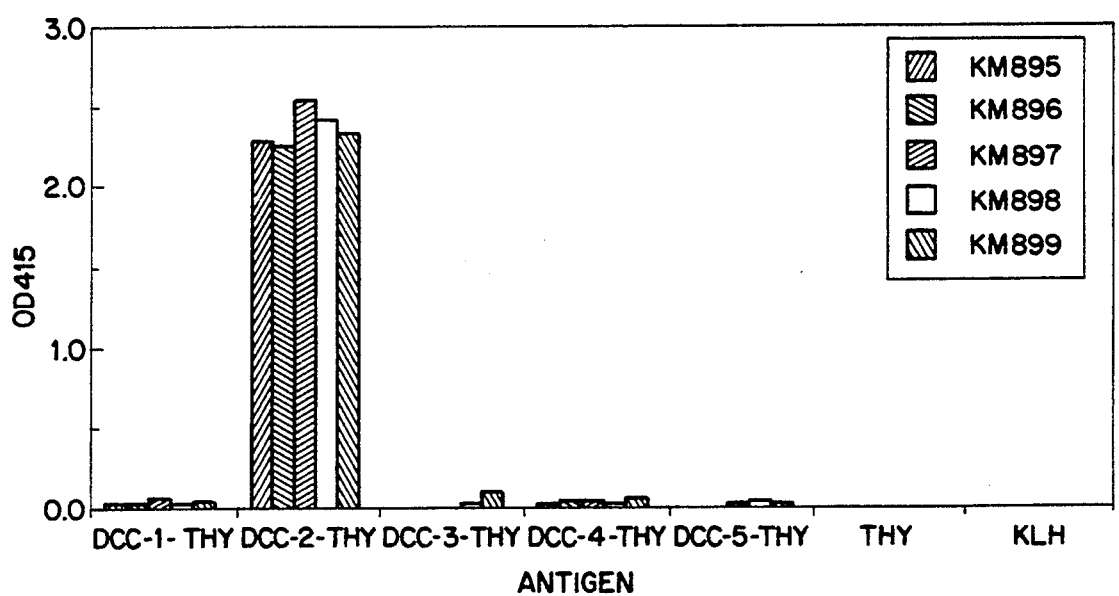

Hybridomas were prepared using 25 mice (5 mice for each peptide). A total of 10 hybridomas producing monoclonal antibodies which were reactive with DCC-2-THY but not with peptide-THY conjugates other than DCC-2-THY were selected from hybridomas prepared from a mouse that had been immunized with DCC-2, and the thus selected hybridomas were designated KM890 to KM899. Reactivities of hybridomas KM890 to KM894 with each peptide-THY are shown in FIG. 1 (a), and those of the hybridomas KM895 to KM899 in FIG. 1 (b). Such hybridomas producing monoclonal antibodies reactive with DCC-2-THY but not with peptide-THY conjugates other than DCC-2-THY were not found in about 50,000 hybridomas prepared from 24 other mice.

Subclasses of hybridomas KM890 to KM899 were determined by enzyme immunoassay using a mouse subclass typing kit (Zymed Laboratories), with the results shown in Table 1.

TABLE 1

| Monoclonal antibody | Subclass |
|---|---|
| KM890 | IgG3 |
| KM891 | IgG3 |
| KM892 | IgG3 |
| KM893 | IgG3 |
| KM894 | IgG2a |
| KM895 | IgG2a |
| KM896 | IgG2a |
| KM897 | IgG2a |
| KM898 | IgG2a |
| KM899 | IgG2a |

(5) Purification of monoclonal antibodies

The hybridoma cell lines KM890 to KM899 obtained as described in the above step (4) were administered to pristane-treated female nude mice of 8 weeks of age by intraperitoneal injection at a dose of 5 to 10×10⁶ cells per animal. The hybridomas caused ascites tumors within 10 to 21 days. The ascitic fluid was collected from each ascitic fluid-carrying mouse (1 to 8 ml per animal) and centrifuged (3,000 rpm, 5 minutes) for removing solid matter. The resulting supernatant was subjected to two repetitions of salting out effected with 50% ammonium sulfate and 40% ammonium sulfate, respectively, then dialyzed against 0.04M phosphate buffer (pH 8.0) containing 0.03M sodium chloride and applied to a DEAE Sepharose (Whatman DE52) column, followed by elution with 0.04M phosphate buffer (pH 8.0) containing 1.0M sodium chloride. Thus, an IgG fraction was collected to give a purified monoclonal antibody.

(6) Selection of anti-DCC gene product specific monoclonal antibodies

Staining of large bowel cancer tissue sections derived from a formalin-fixed paraffin-embedded specimen was carried out in the following manner using the monoclonal antibodies obtained in the above step (5) as the first antibody in immunohistochemical staining.

A section having a thickness of 4 μm was prepared from the paraffin-embedded specimen using a microtome, put on a silane-coated slide glass (Matsunami Co., Ltd.), treated with xylene to remove paraffin and then treated with ethanol to make the section hydrophilic. The thus treated section was washed with PBS, subjected to blocking with methanol containing 0.3% hydrogen peroxide and 10% rabbit serum solution and then allowed to react, at 4° C. for 10 hours, with the purified monoclonal antibodies (10 μg/ml) obtained in the above step (5) as the first antibody. After washing with PBS, the resulting section was allowed to react with a second antibody (biotin-labeled mouse antibody, Nichirei Corp.) at room temperature for 90 minutes and then with peroxidase-labeled streptoavidin (Nichirei Corp.) at room temperature for 5 minutes. The thus treated tissue section was subjected to color development using a diaminobenzidine solution and then to chromosomal staining with Methyl Green, followed by dehydration and sealing and subsequent observation under a microscope. The results demonstrated that KM890 was effective for positive staining of the cancer cells, while KM891 to KM899 showed lower frequency for positive staining in comparison with KM890. In addition, KM890 did not react with other peptides such as motilin, motilin derivatives and the like.

(7) Application to histological tissue examination

Formalin-fixed paraffin-embedded specimens of 31 large bowel cancer cases (29 cases of advanced stage cancer and 2 cases of early cancer) were subjected to immunohistochemical staining using KM890 as the first antibody. Cancer cells were found to be positive in 8 cases of the advanced large bowel cancer. Positive staining was observed in intracellular portions and on cell membranes of the cancer cells. In addition, staining was negative in the case of benign lesions of tubular adenoma and chorionic adenoma. Thus, it appears that the DCC gene product accumulates in excess amounts in the case of advanced large bowel cancer.

Thus, anti-DCC gene product monoclonal antibodies according to the present invention are useful in cancer diagnosis.

While the invention has been described in detail and with reference to specific examples thereof, it will be apparent to one skilled in the art that various changes and modifications can be made therein without departing from the spirit and scope thereof.

What is claimed is:

1. A method of screening for the presence of cancer cells in a large bowel tissue sample comprising contacting said sample with monoclonal antibodies, or binding fragments thereof, which are specifically reactive with a peptide encoded by a tumor suppressor gene DCC, wherein said antibodies are mouse monoclonal antibodies KM890 belonging to the IgG3 subclass, wherein said contacting is effected under conditions such that said monoclonal antibodies can bind to the peptide product of the tumor suppressor gene DCC present in said sample, elevated levels of the peptide product of the tumor suppressor gene DCC being associated with the presence of carcinoma of the large bowel, whereby a complex is formed, and detecting the presence of said complex, the presence of said complex being indicative of the presence of cancer cells in said sample.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:1:

```
Ala  Phe  Met  Gly  Asp  Thr  Val  Leu  Leu  Lys  Cys  Glu  Val  Ile  Gly  Glu
1                 5                          10                         15
Pro  Met  Pro  Thr  Ile
                20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
    ( A ) ORGANISM: Homo sapiens ( x i ) SEQUENCE DESCRIPTION: SEQ ID NO:2:

```
Leu Gln Pro Gly Asp Ile Gly Ile Tyr Arg Cys Ser Ala Arg Asn Pro
1               5                   10                  15

Ala Ser Ser Arg Thr
            20
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:3:

```
Phe Thr Val Phe Phe Ser Arg Glu Gly Asp Asn Arg Glu Arg Ala Leu
1               5                   10                  15

Asn Thr Thr Gln
            20
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:4:

```
Val Ala Tyr Asn Glu Trp Gly Pro Gly Glu Ser Ser Gln Pro Ile Lys
1               5                   10                  15

Val Ala Thr Gln
            20
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:5:

```
Thr Gly Tyr Lys Ile Arg His Arg Lys Thr Thr Arg Arg Gly Glu Met
1               5                   10                  15
```

Glu Thr Leu Glu
20